United States Patent
Fairley et al.

(10) Patent No.: US 10,881,534 B2
(45) Date of Patent: Jan. 5, 2021

(54) MODULAR LOWER LIMB PROSTHESIS SYSTEM

(71) Applicants: Joseph Fairley, Saratoga Springs, NY (US); Henry Warder, New York, NY (US); Joshua Coutts, Victoria (CA)

(72) Inventors: Joseph Fairley, Saratoga Springs, NY (US); Henry Warder, New York, NY (US); Joshua Coutts, Victoria (CA)

(*) Notice: Subject to any disclaimer, the term of this patent is extended or adjusted under 35 U.S.C. 154(b) by 223 days.

(21) Appl. No.: 15/947,444

(22) Filed: Apr. 6, 2018

(65) Prior Publication Data

US 2018/0289511 A1 Oct. 11, 2018

Related U.S. Application Data

(60) Provisional application No. 62/483,372, filed on Apr. 8, 2017.

(51) Int. Cl.
| | |
|---|---|
| A61F 2/66 | (2006.01) |
| A61F 2/80 | (2006.01) |
| A61F 2/64 | (2006.01) |
| A61F 2/60 | (2006.01) |
| A61F 2/50 | (2006.01) |

(52) U.S. Cl.
CPC ............ *A61F 2/66* (2013.01); *A61F 2/5046* (2013.01); *A61F 2/60* (2013.01); *A61F 2/64* (2013.01); *A61F 2/644* (2013.01); *A61F 2/80* (2013.01); *A61F 2002/505* (2013.01); *A61F 2002/5056* (2013.01); *A61F 2002/5083* (2013.01); *A61F 2002/6642* (2013.01); *A61F 2002/6657* (2013.01); *A61F 2002/6671* (2013.01)

(58) Field of Classification Search
CPC ...... A61F 2/64; A61F 2/66; A61F 2002/5056; A61F 2002/5093; A61F 2002/6642; A61F 2002/6657; A61F 2002/6671; A61F 2/80; A61F 2/76; A61F 2/644; A61F 2/604; A61F 2/5046; A61F 2/5044; A61F 2002/505; A61F 2002/5087
See application file for complete search history.

(56) References Cited

U.S. PATENT DOCUMENTS

| | | | | |
|---|---|---|---|---|
| 5,653,768 | A * | 8/1997 | Kania | A61F 2/66 623/27 |
| 6,398,817 | B1 * | 6/2002 | Hellberg | A61F 2/76 623/33 |
| 2012/0310372 | A1 * | 12/2012 | Omarsson | A61F 2/644 623/43 |
| 2016/0058580 | A1 * | 3/2016 | Bartlett | A61F 2/642 623/46 |

OTHER PUBLICATIONS

Black, Sarah. 3D printing continuous carbon fiber composites? (Year: 2014).*

* cited by examiner

*Primary Examiner* — Christie L Bahena
(74) *Attorney, Agent, or Firm* — Bond Schoeneck and King PLLC; David Nocilly

(57) ABSTRACT

A lower limb modular prosthetic system that may be fabricated by a 3D printer capable of printing with composite fiber filament, nylon, or metal. The production process may include a 3D printer that is capable of routing fiber in specifically programmed patterns. The components of the prosthetic system may be designed for direct patient end-use, and may be energy returning in nature.

17 Claims, 21 Drawing Sheets

MODULAR LOWER LIMB PROSTHESIS SYSTEM

BACKGROUND OF THE INVENTION

1. Field of the Invention

The present invention relates to prosthesis and, more particularly, to a design for a lower limb prosthesis fabricated from composite filament using a three-dimensional printer.

2. Description of the Related Art

Three-dimensionally (3D) printed parts have previously faced numerous constraints on structural integrity for physical applications. Traditional 3D printed materials in the form of spooled plastic filament cannot produce parts strong enough to withstand the stresses and strains of dynamic loads, such as those experienced in human gait mechanics. The shear forces of sudden movement, as well as the need for a dynamic elastic response (DER) in certain types of prosthetic components, limit the composition of materials that can support walking motion over an extended period of time. Traditionally, components of lower limb prostheses are fabricated with materials such as carbon fiber, fiberglass, stainless steel, and titanium.

A preferred method of 3D printing is known as composite filament fabrication (CFF). CFF is a process which allows for fabrication of 3D printed parts which may be reinforced with materials such as continuous strands of carbon fiber and fiberglass. By utilizing materials such as continuous carbon fiber and fiberglass to reinforce 3D printed components, designs may possess increased strength properties.

The biomechanical performance of a novel 3D printed modular lower limb prosthetic system may mirror that of a conventional energy storing and returning (ESR) lower limb prosthesis during a normal gait cycle. Traditionally, an ESR prosthetic foot is preferred for its DER. Other prosthetic feet, such as the solid ankle-cushioned heel (SACH), do not possess DER. DER is superior and preferred because it requires less effort to be provided from the amputee in order to walk. The amputee can walk further and for greater periods of time with less energy input. As an amputee begins the gait cycle with initial contact, or heel strike, a dynamic load is placed on the heel portion of the prosthetic foot. The load, or energy, derives from the force of the weight of the amputee applied to the prosthetic foot. The energy is stored within the heel until the amputee transitions through midstance, where both the heel and toe are on the ground. Finally, the stored energy is returned during toe-off, and provides a propulsion force through the end of the gait cycle.

As a result of the limitations in the materials and processes used, previous attempts at 3D printing lower limb prostheses have not been viable for long-term patient end-use. The attempts have utilized various forms of 3D printing, including fused-deposition modeling (FDM) and selective laser sintering (SLS). These processes and their corresponding materials pose structural limitations to the printed parts. The layering technique of FDM is not consistently accurate and may result in weak interlayer bonding or warping. This is common with plastic 3D printing filament if the printing settings are not exactly precise, or if the material has been compromised by moisture. The process of SLS does not allow for continuous fiber to be integrated within the part. Instead, fiber powder is mixed with the main plastic material. As a result, there is a need for a design that can solve these issues by allowing for the 3D printing of continuous fiber filament to provide superior structural complexity and durability for long-term patient end-use.

BRIEF SUMMARY OF THE INVENTION

The invention is a prosthetic fabrication approach wherein the major components are formed from a composite filament defining a series of concentric layers. The component may be a body having a core surrounded by the series of concentric layers. The core may be surrounded by at least six concentric layers of composite filament. The body may include a mounting portion configured for attachment to a component of a prosthetic system. The mounting portion may comprise a pair of passages extending laterally through the body and a series of openings extending transversely to and in communication with the pair of passages. The body may comprise a foot having a heel and a forefoot interconnected by a first curved portion. The mounting portion may be interconnected to the heel and forefoot by a second curved portion. The body may comprise a pair of corresponding knee sections, wherein one of the pair of corresponding knee sections includes the mounting portion and the other of the pair of corresponding knee sections includes a second mounting portion. The pair of knee sections may be interconnected by a four bar mechanism and include a cable flexion inhibitor extending therebetween and embedded therein. The body may also comprise a pylon with the series of concentric layers extending longitudinally within the pylon. A socket may be interconnected to the pylon.

The present invention may also include a comprehensive system of a foot formed from a first composite filament defining a first series of concentric layers and having a first mounting portion and a pylon formed from a second series of concentric layers extending longitudinally therein interconnected to the first mounting portion. A socket interconnected to the pylon, or a pair of knee sections, wherein one of the pair of knee sections is interconnected to the pylon. In the latter case, a socket may be interconnected to the other of the knee sections. The pair of knee sections may be interconnected by a four bar mechanism and a cable flexion inhibitor embedded therein.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 7:
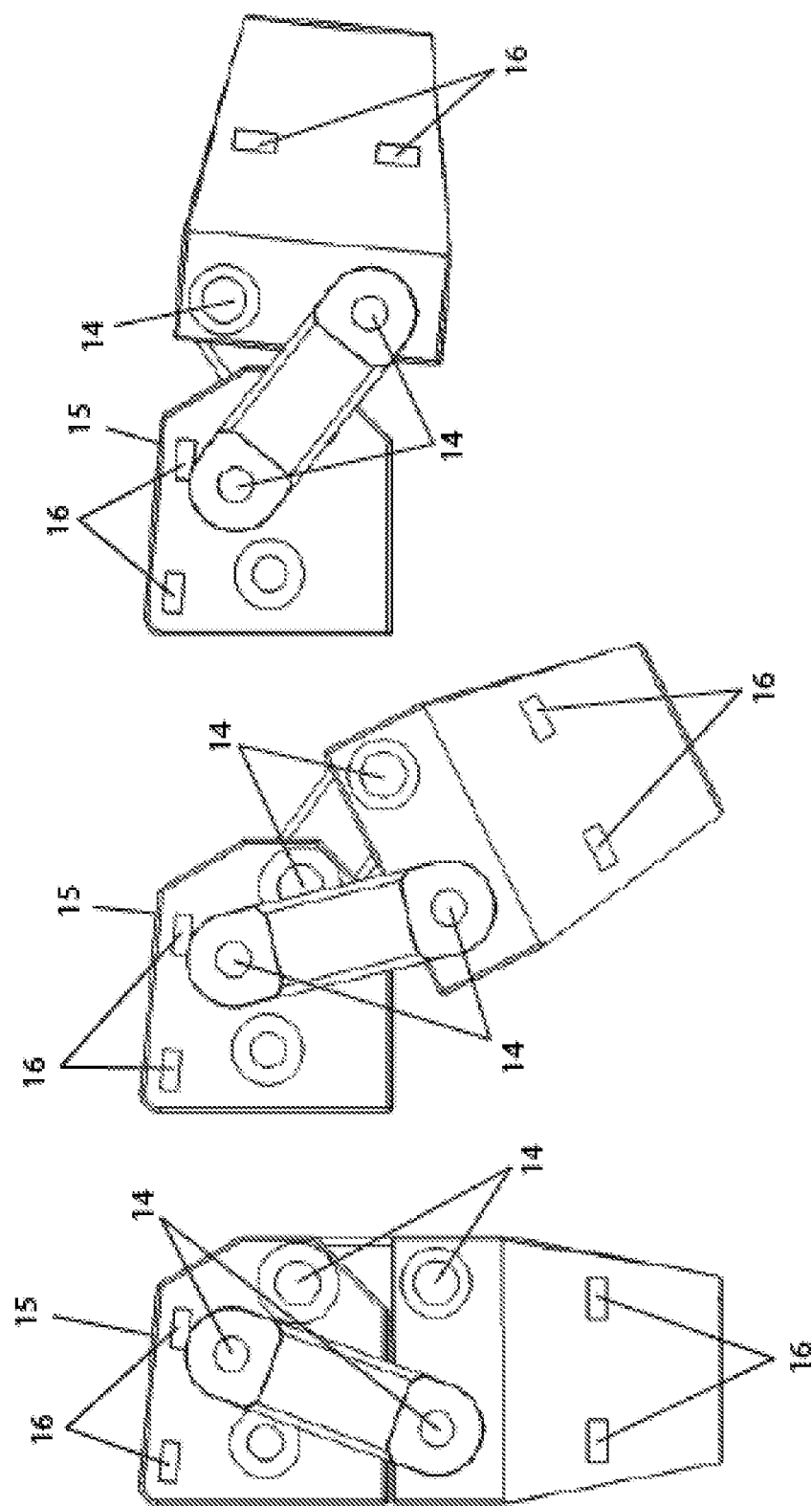

FIG. 7 demonstrates various positions of an embodiment of a prosthetic knee.

Figure 8:
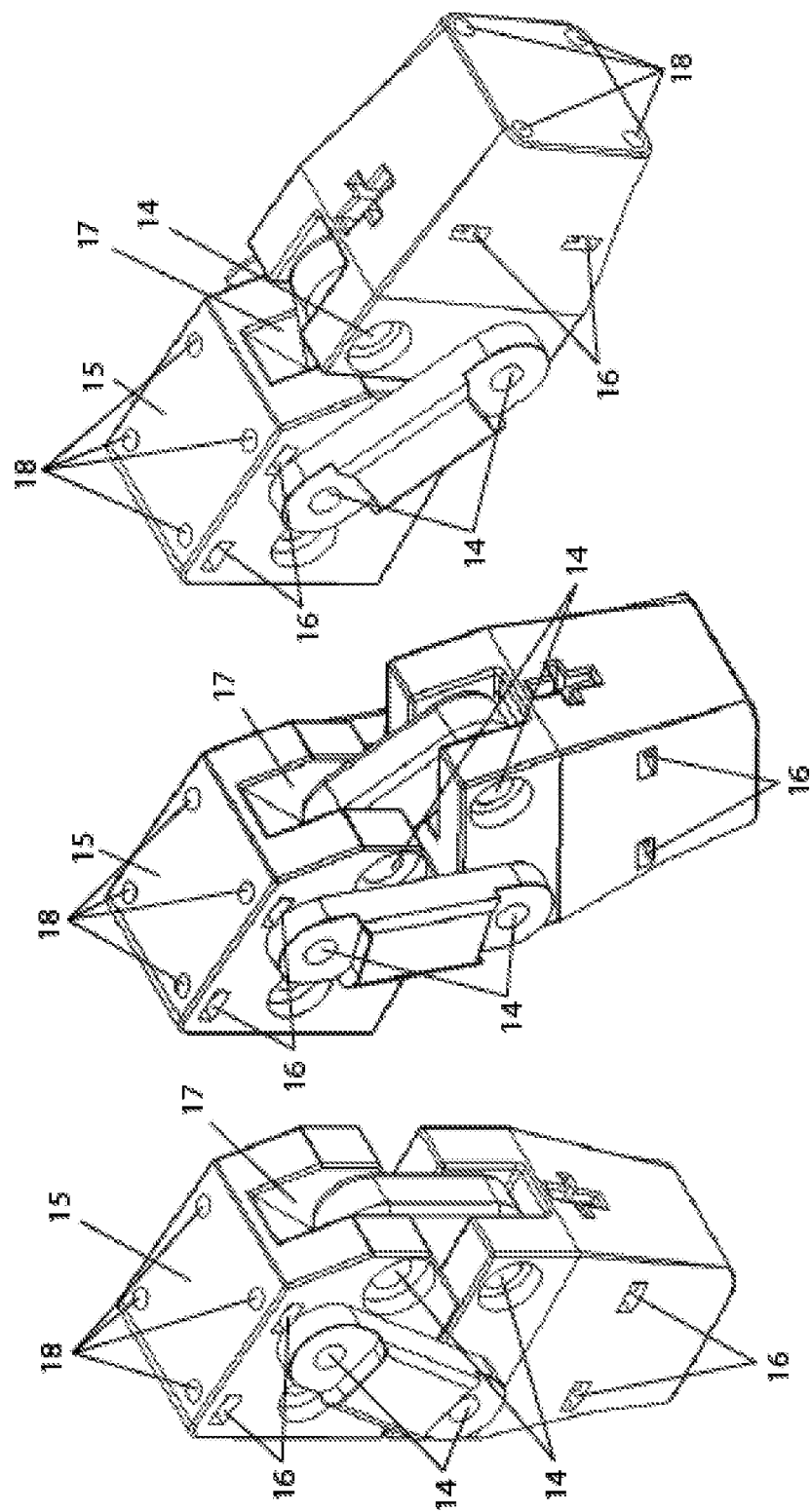

FIG. 8 is an isometric view of various positions of an embodiment of a prosthetic knee.

Figure 9:
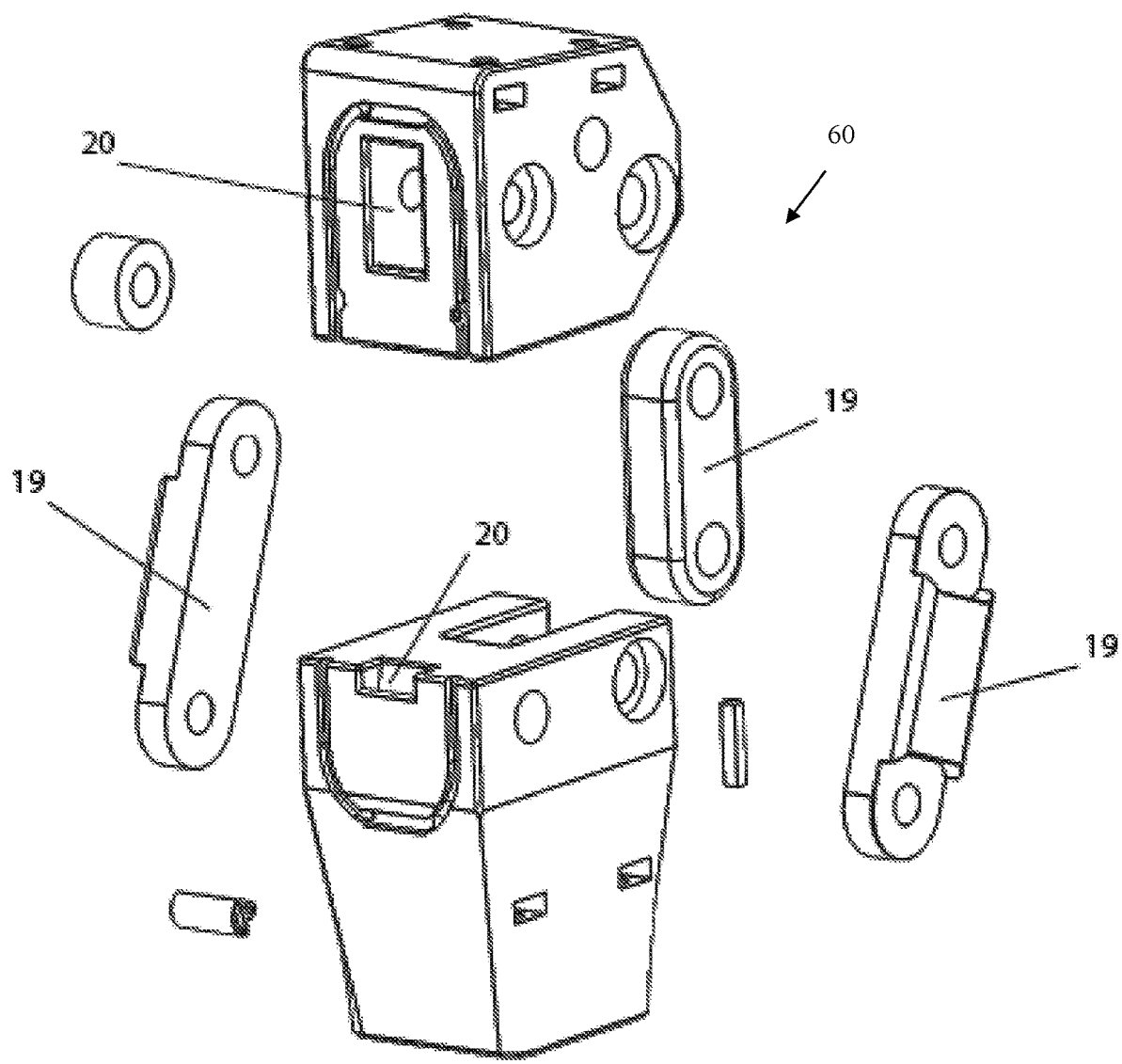

FIG. 9 is an exploded assembly of an embodiment of a prosthetic knee.

Figure 10:
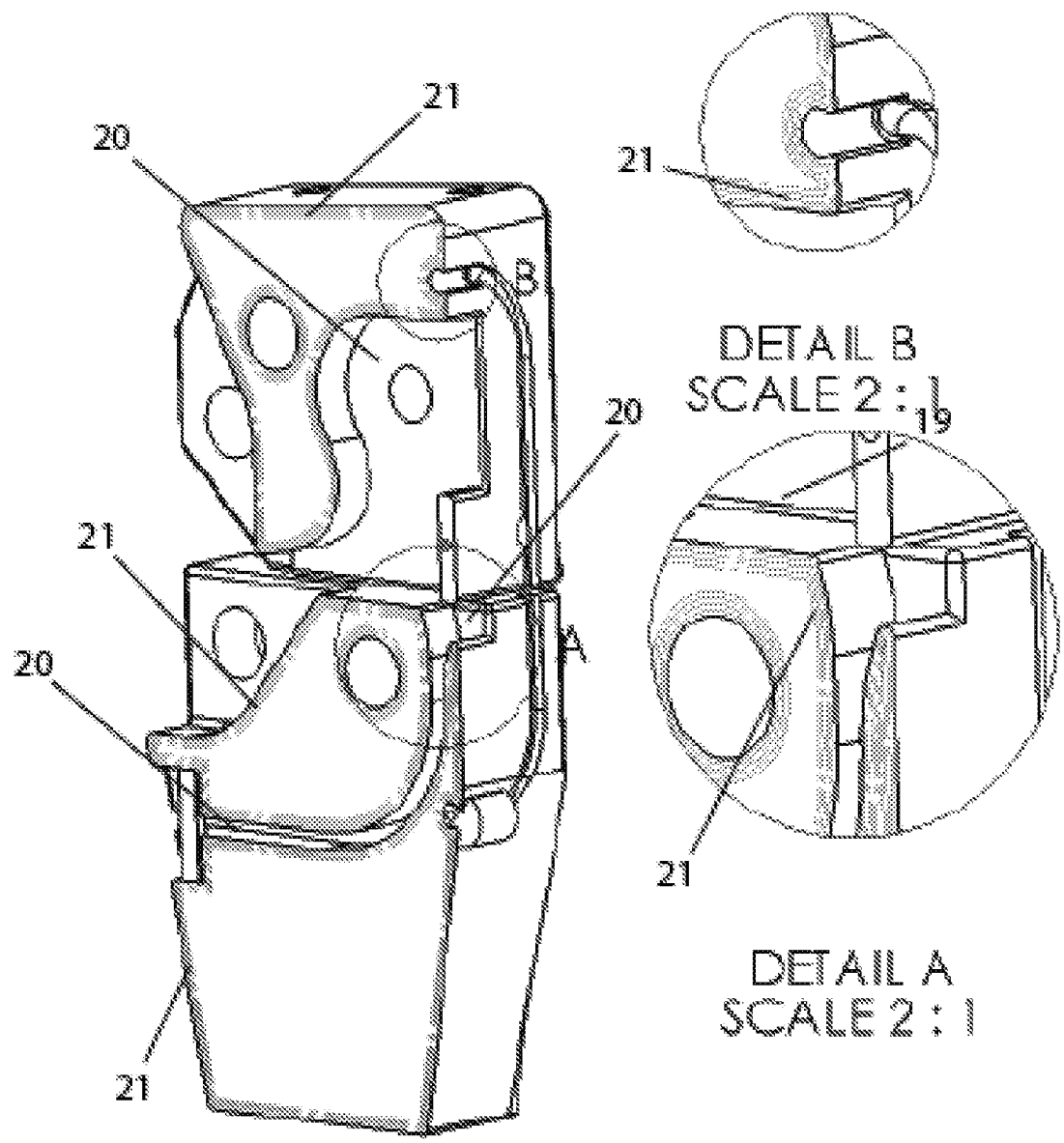

FIG. 10 is an isometric cross sectional view of an embodiment of a prosthetic knee.

Figure 11:
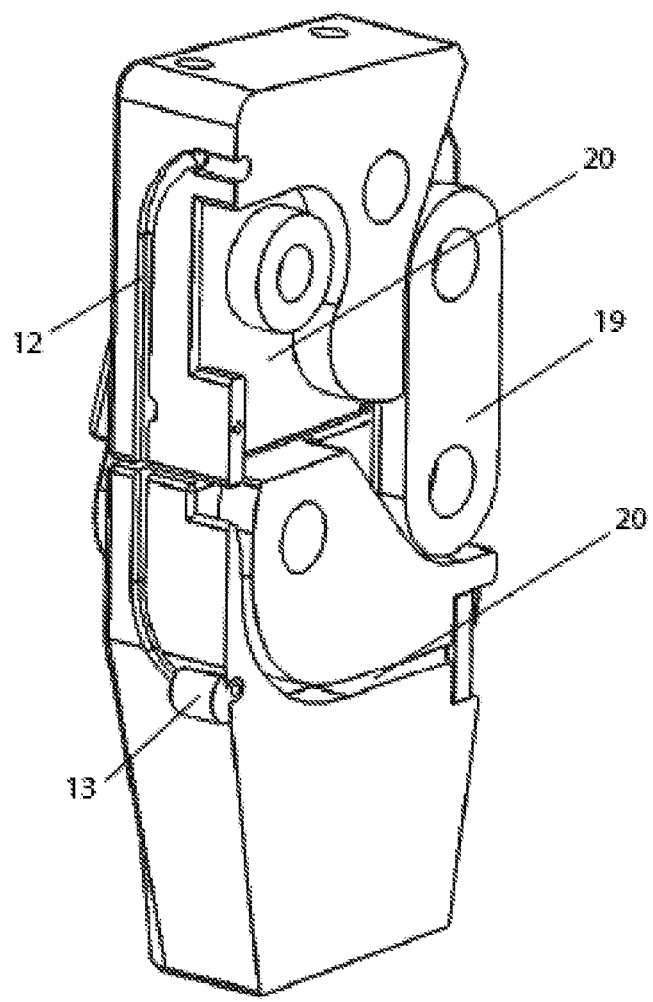

FIG. 11 is an isometric cross sectional view of an embodiment of a prosthetic knee.

Figure 12:
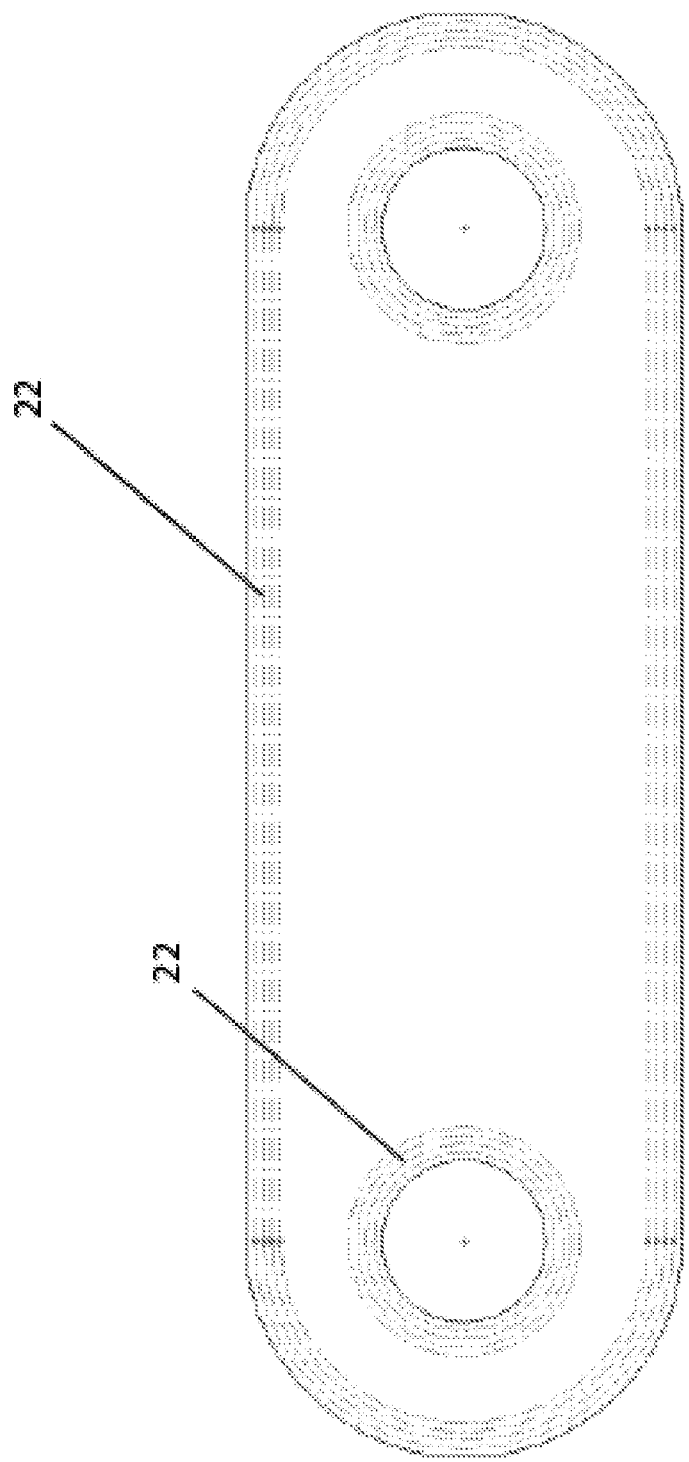

FIG. 12 is a cross sectional side view of an embodiment of a prosthetic knee component.

Figure 13:
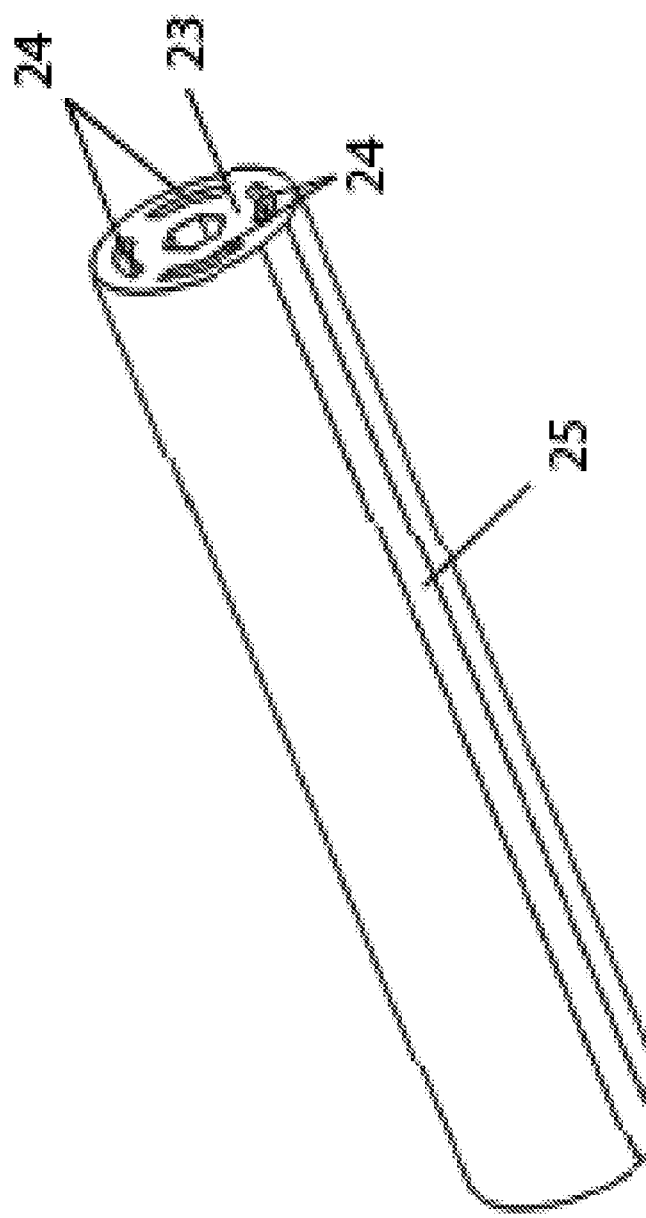

FIG. 13 is an isometric view of an embodiment of a prosthetic pylon.

Figure 14:
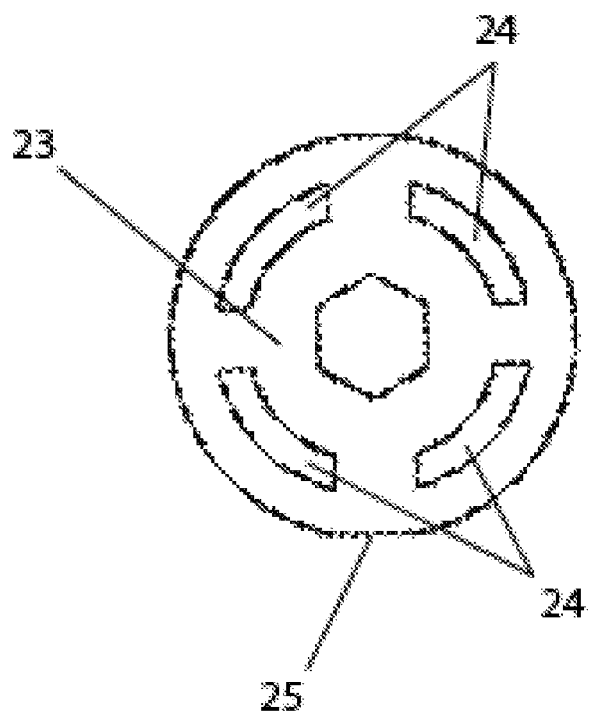

FIG. 14 is a front section view of an embodiment of a prosthetic pylon.

Figure 15:
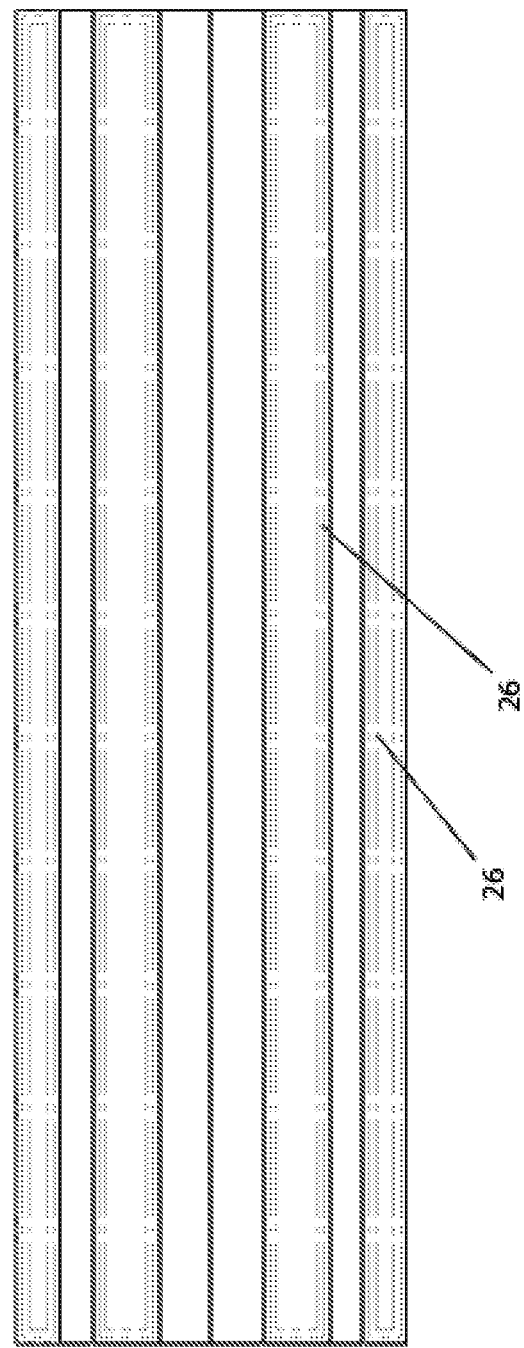

FIG. 15 is a cross section of an embodiment of a prosthetic pylon.

Figure 16:
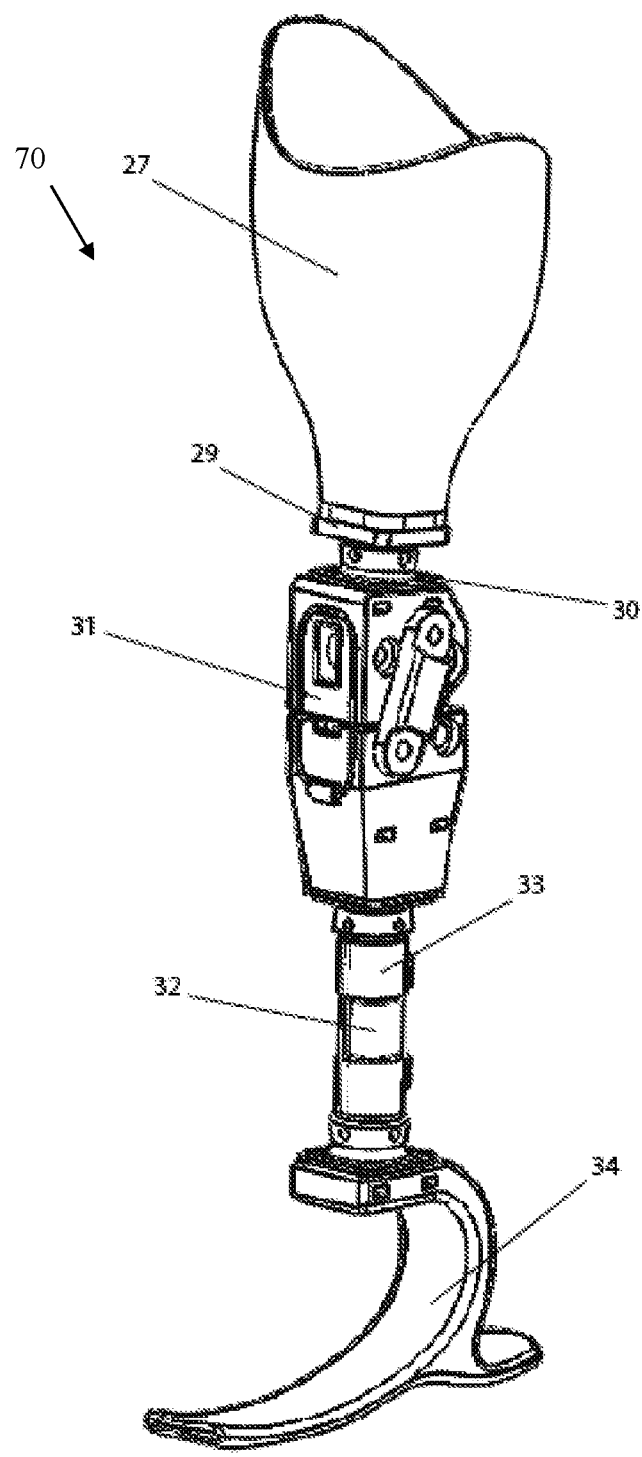

FIG. 16 is an isometric view of a possible embodiment of an above-knee assembled lower limb prosthetic system which may be comprised of modular 3D printed prosthetic components.

Figure 17:
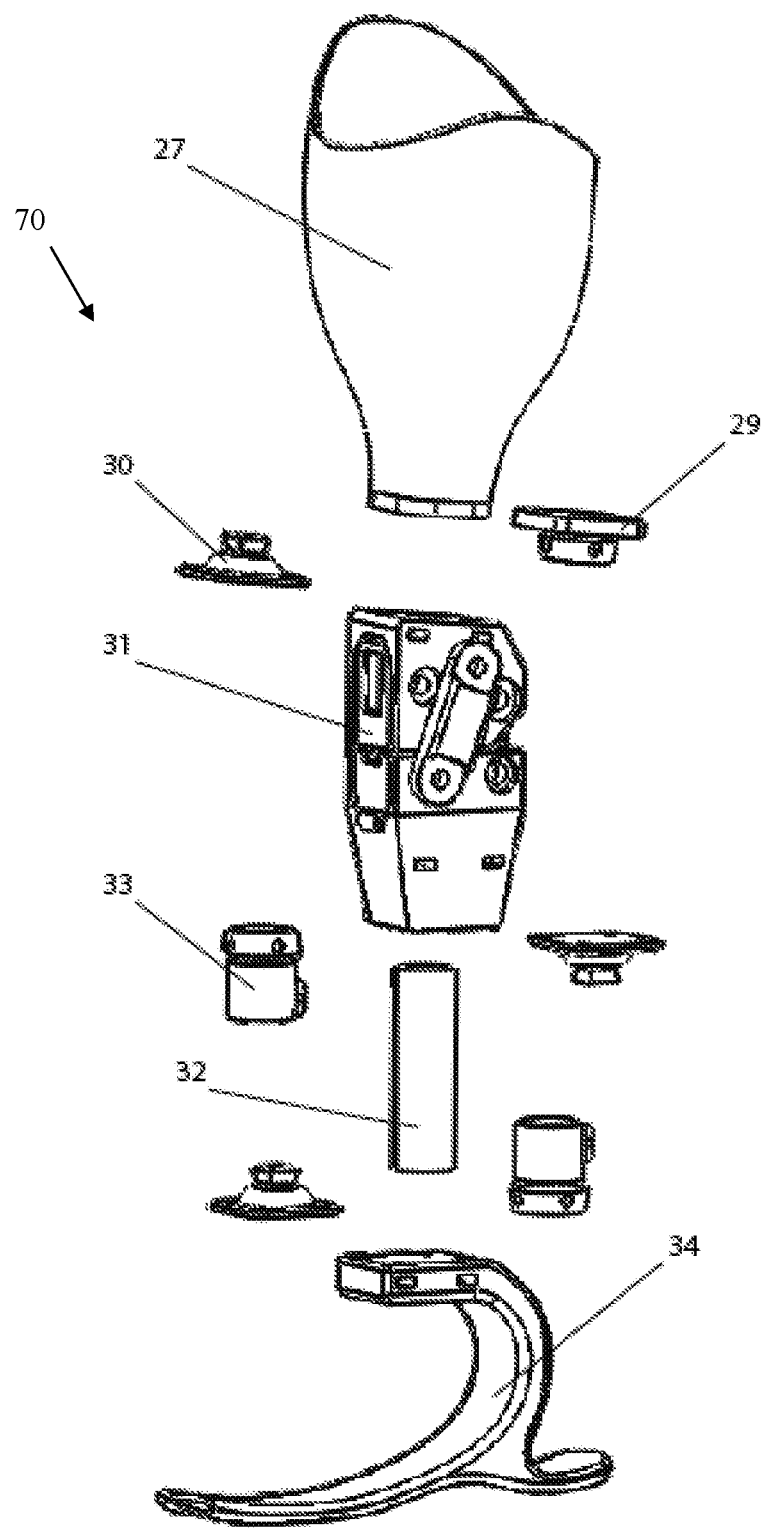

FIG. 17 is an exploded view of a possible embodiment of an above-knee assembled lower limb prosthetic system.

Figure 18:
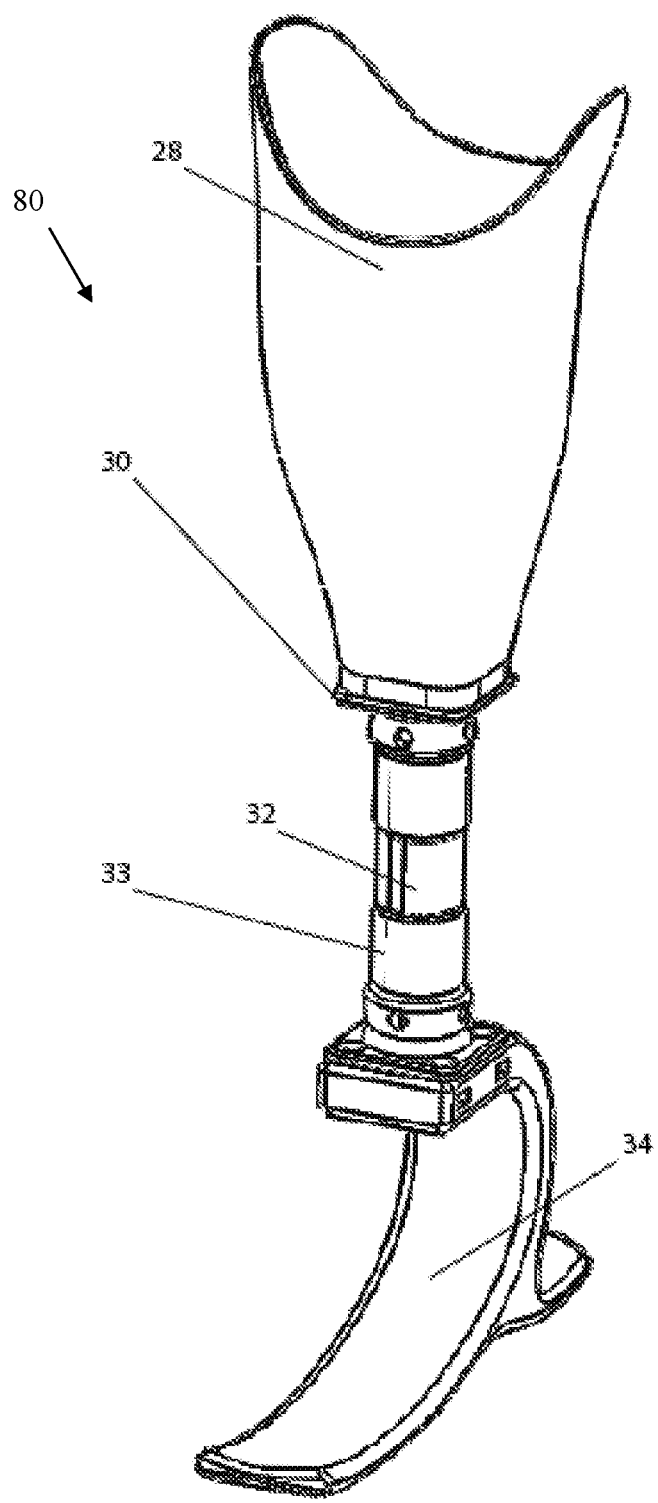

FIG. 18 is an isometric view of a possible embodiment of a below-knee assembled lower limb prosthetic system.

Figure 19:
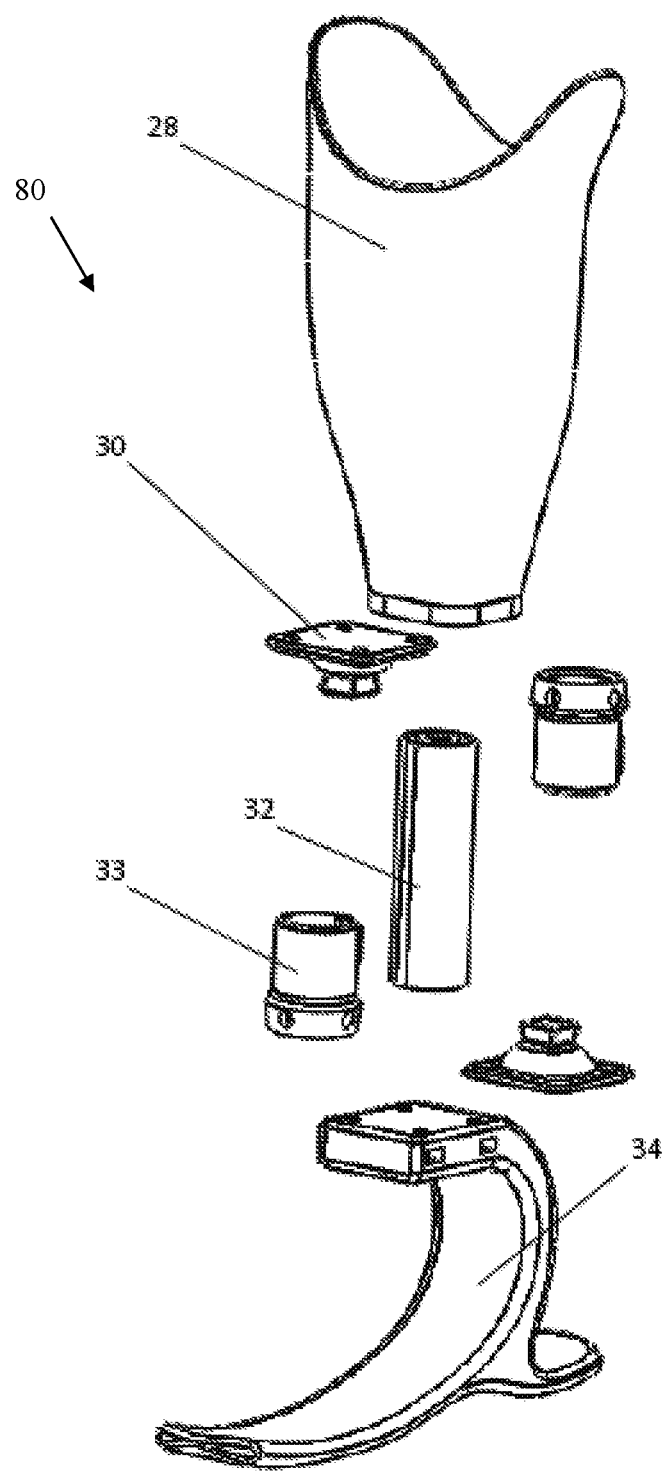

FIG. 19 is an exploded view of a possible embodiment of a below-knee assembled lower limb prosthetic system.

Figure 20:
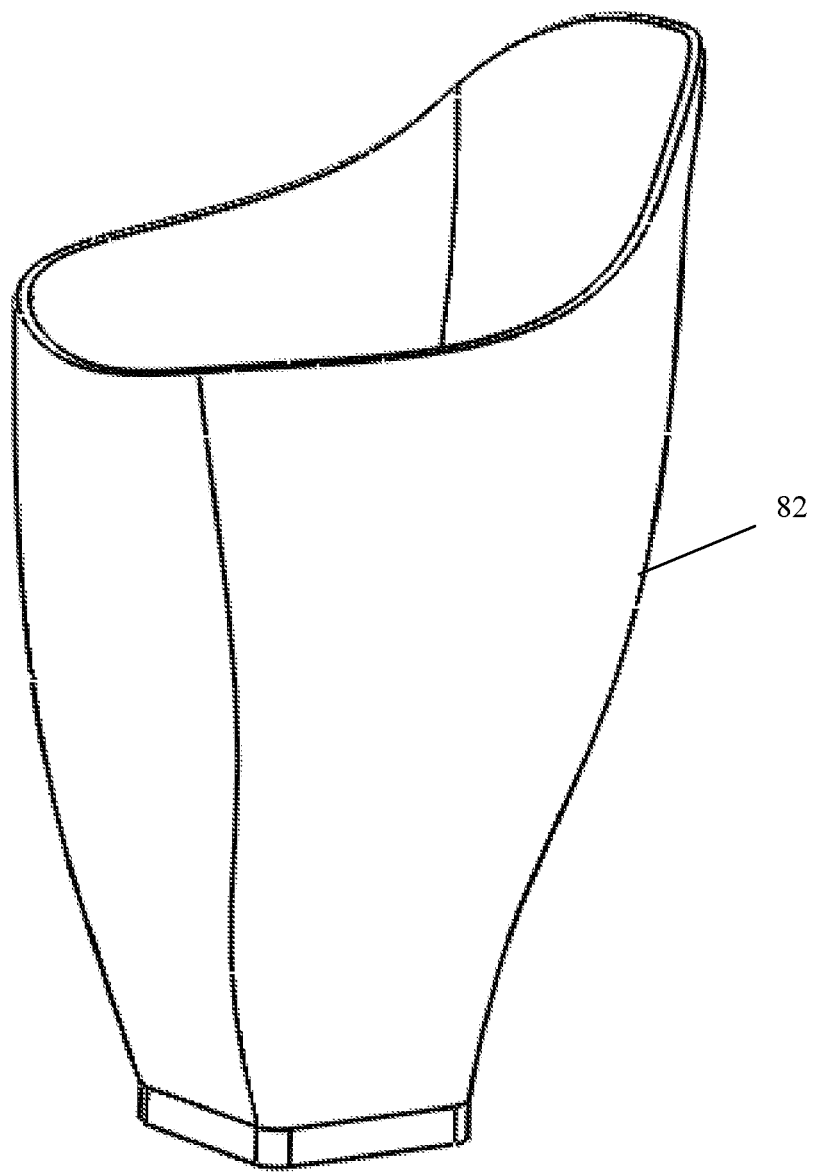

FIG. 20 is an isometric view of an embodiment of an above-knee prosthetic socket.

Figure 21:
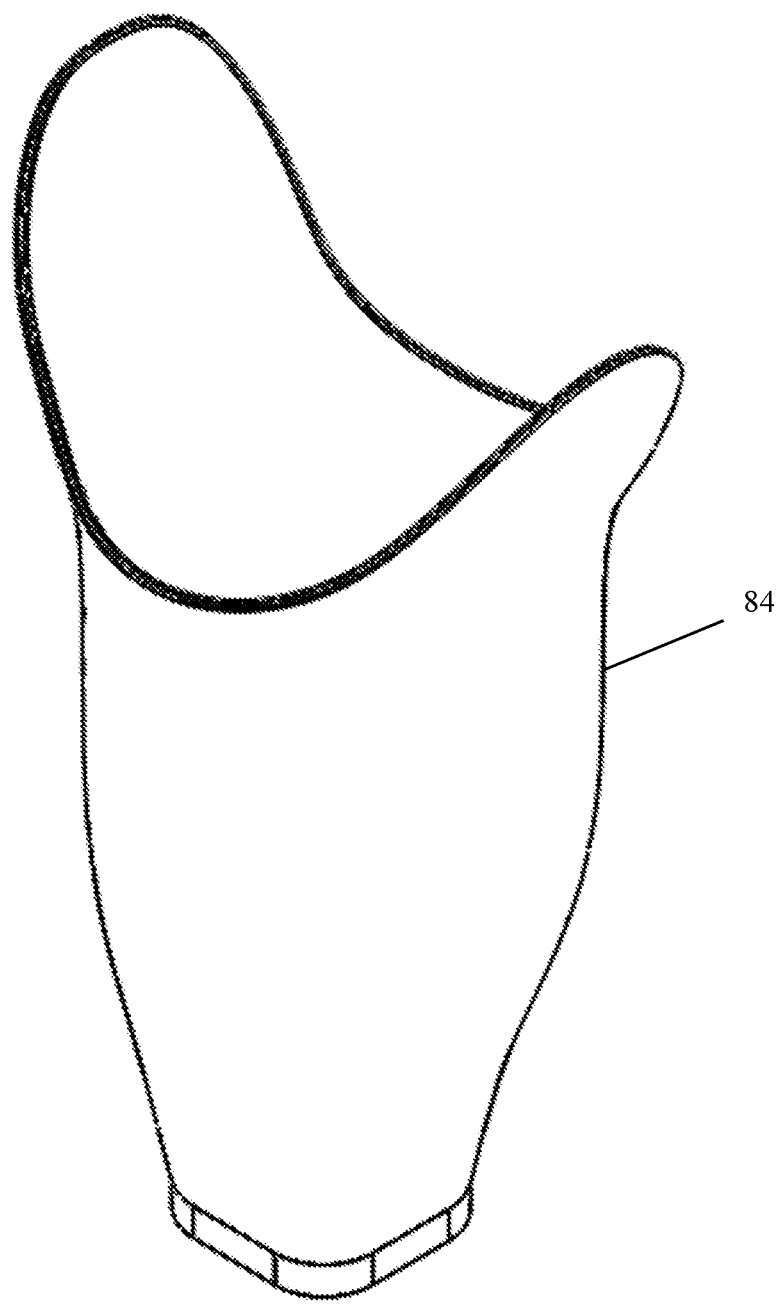

FIG. 21 is an isometric view of an embodiment of an below-knee prosthetic socket.

DETAILED DESCRIPTION OF THE INVENTION

Figure 1:
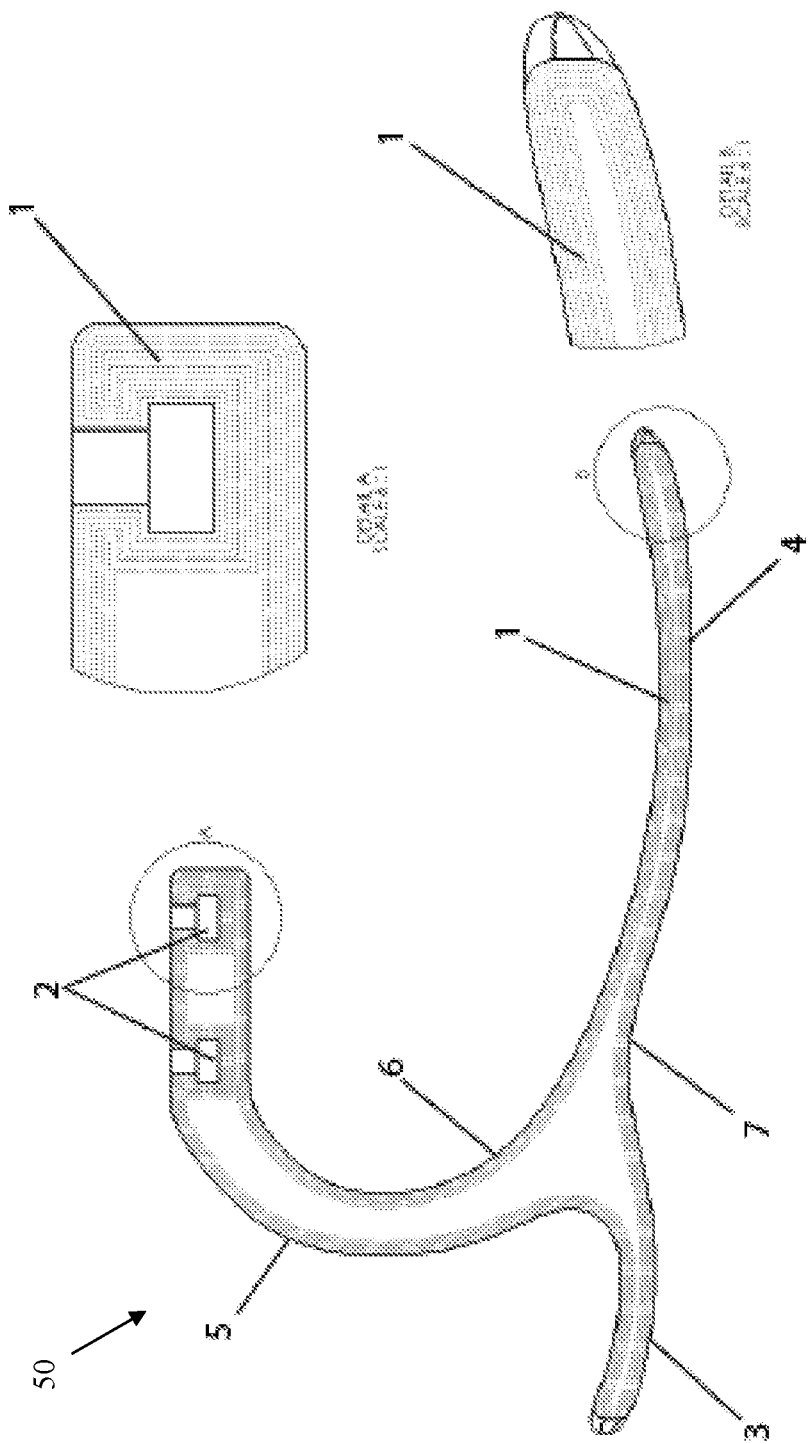
FIG. 1 is a cross sectional view of an embodiment of a prosthetic foot.

Referring to the figures, wherein like numeral refer to like parts throughout, there is seen in FIG. 1, a 3D printed fiber prosthesis foot 50 according to the present invention. The modular lower limb prosthetic components are preferably produced by a 3D printer capable of CFF. The present invention may be fabricated using one or more 3D printers where nylon filament is heated, then extruded onto a buildplate controlled by pre-programmed software settings. At specified layers within the print, fiber material is heated and extruded in the same manner as the nylon. This process continues until the full part is printed. Assembly is required for some components of the system. The components are preferably designed using a 3D design software and then uploaded to slicing software, such as Eiger available from MarkForged, to adapt the design for successful printing. Another aspect of the invention includes the precise specification of the location of the fiber during the printing process using a program or other means.

Referring to FIG. 1, composite fiber 1 is seen as concentric boundary rings which may provide strength and flexibility to prosthesis 50. The specific location of the fiber may be customized by way of specialized programming software. Concentric orientation of the fiber is critical to obtain the necessary structural capabilities and dynamic elastic response from the components. Multiple concentric layers are needed to provide the support for the biomechanical forces during ambulation, and their positioning within the component is critical. Placing the fibers in parallel to the plane of motion allows a dynamic elastic response from the component. Fiber may also be placed in certain locations that require reinforcement for the insertion of machined components.

In one embodiment, two channels 2 may be included in the design and fabricated at the top of prosthesis 50 to accommodate any necessary machined components for coupling of foot 50 to the rests of a prosthetic system, such as that described herein. The heel 3 and forefoot 4 of prosthesis 50 are formed as solid landing structures that may enhance the stability of the user throughout the gait cycle. Large curved surfaces 5, 6, and 7 interconnect channels 2, heel 3 and forefoot 4 to further contribute toward its DER and flexibility of prosthesis 50.

Figure 2:
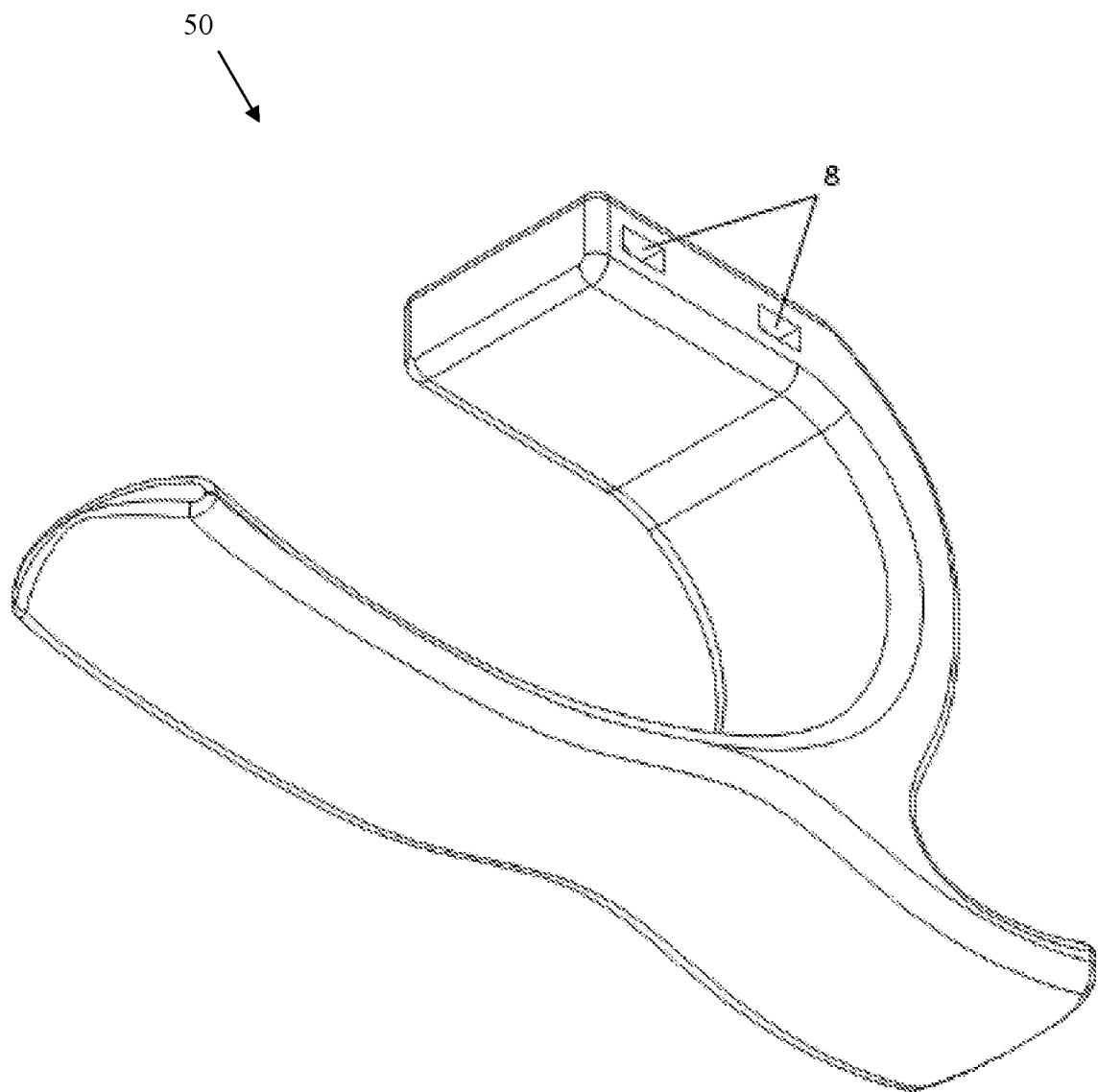
FIG. 2 is an isometric view of an embodiment of a prosthetic foot.
Figure 3:
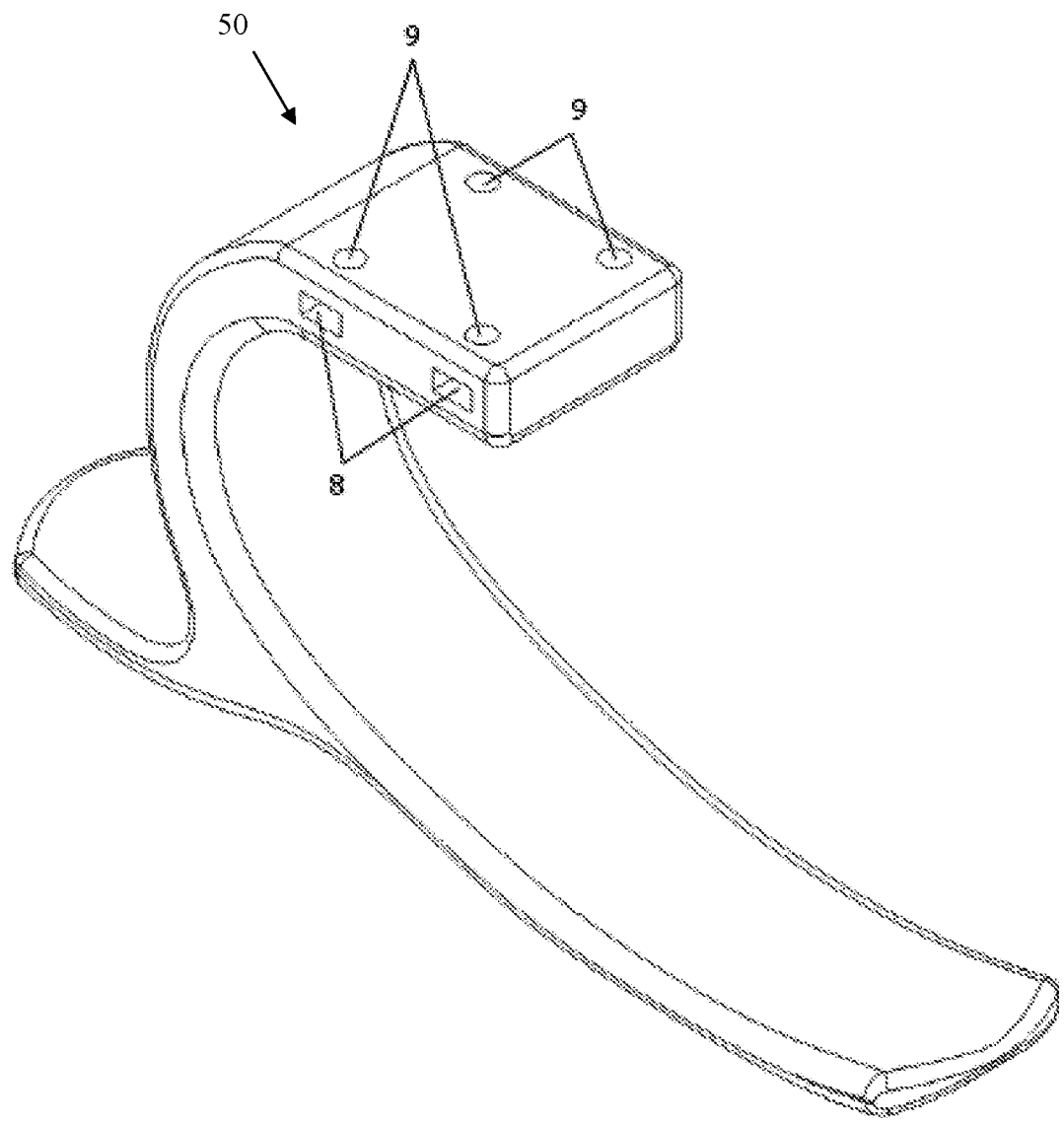
FIG. 3 is an isometric view of an embodiment of a prosthetic foot.
Figure 4:
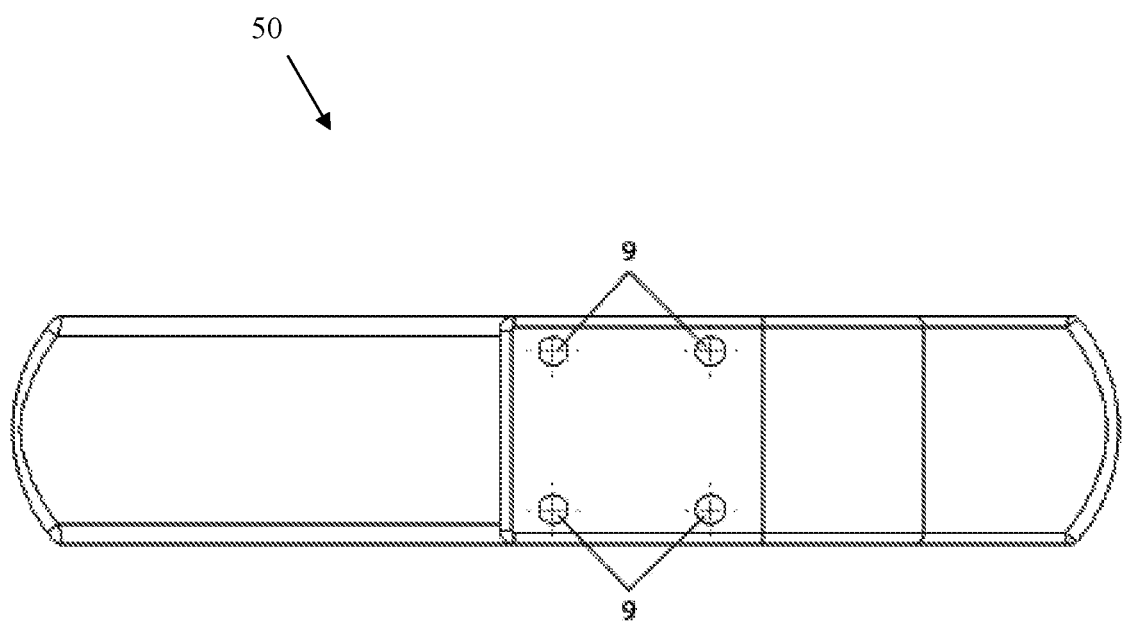
FIG. 4 is a top view of an embodiment of a prosthetic foot.

Referring to FIG. 2, prosthesis 50 includes insertion sites 8 associated with channels 2 for insertion of the machined components used connection of prosthesis 50 to the supporting assembly. As seen in FIGS. 3 and 4, multiple attachment sites 9 may be included for coupling to a machined modular prosthetic part.

Figure 5:
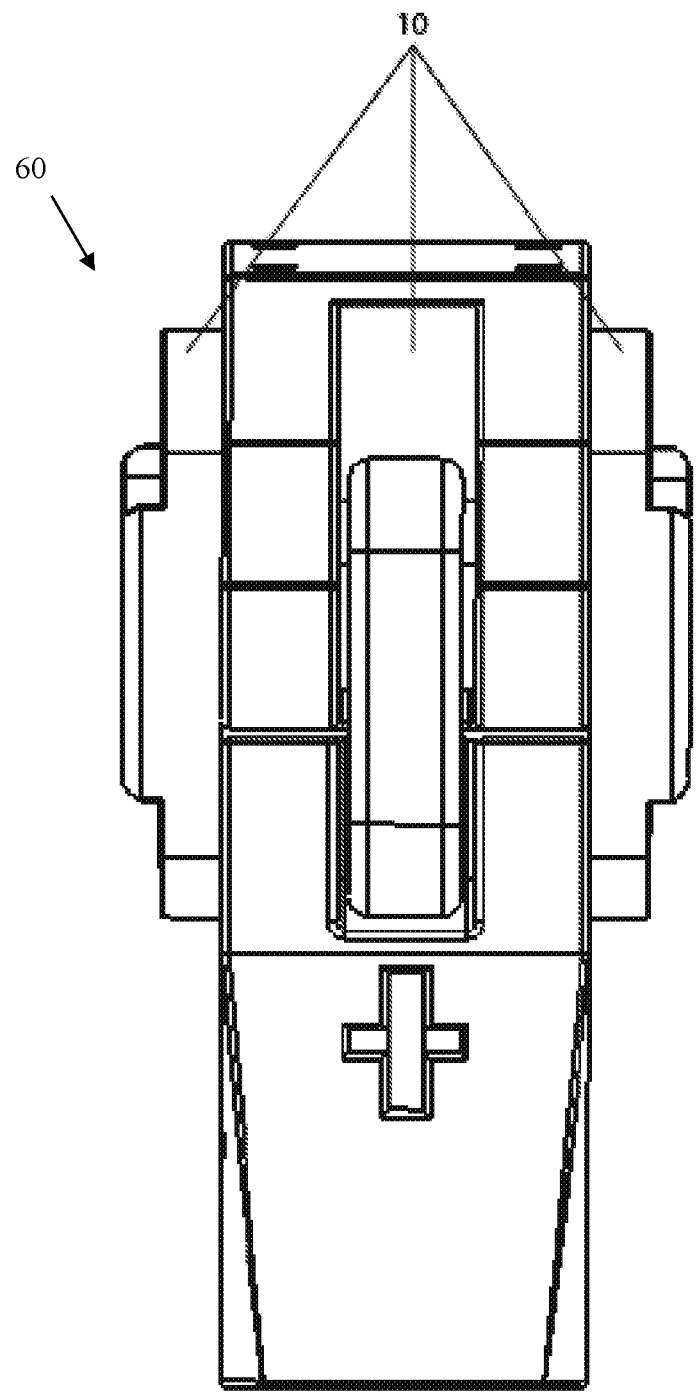
FIG. 5 is a rear view of an embodiment of a prosthetic knee.
Figure 6:
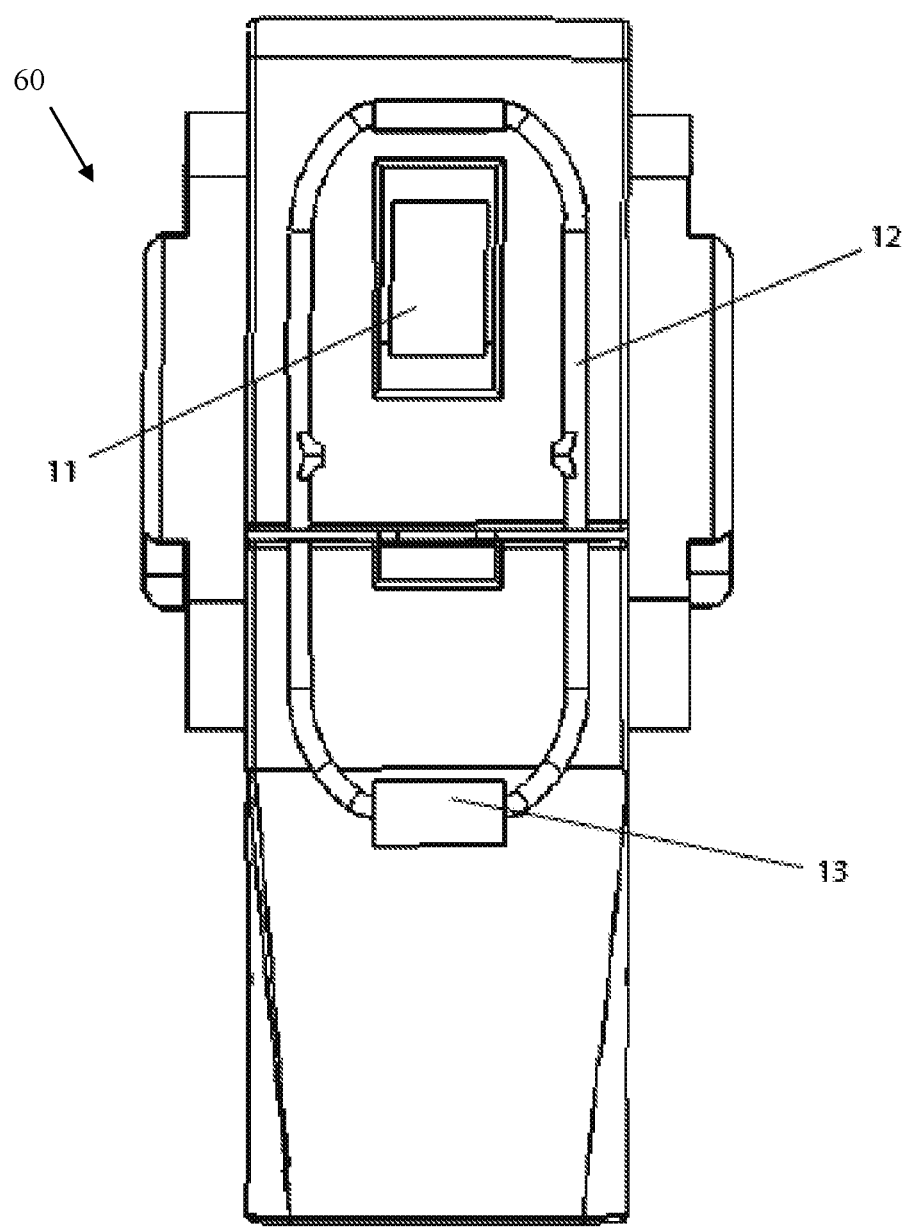
FIG. 6 is a frontal view of an embodiment of a prosthetic knee.

Referring to FIG. 5, the present invention also includes a 3D printed modular prosthetic knee 60. Knee 60 comprises upper and lower sections interconnected with three bars 10, i.e., two bars 10 positioned oppositely and externally of upper and lower sections and a central bar 10 positioned centrally within upper and lower sections. As seen in FIG. 6, knee 60 may include flexion and extension features such as a mount 11 for securing a spring loaded assisted extension system that, for example, may be driven by a coil spring to assist in extending the knee during the gait phase and thus aid in the flexion and extension of the prosthetic knee. Such an assistive mechanism may be comprised of spring loaded extension system, driven by a coiled constant force spring which engages during the gait phase, or by a collection of elastic cables that when flexed, pull the knee from flexion into extension during gait, or by a similar spring or cable driven method. Knee 60 may also include a cable style flexion inhibitor 12 that extends from the upper section and is secured to a retainer 13 located within lower section of knee 60 to prevent over extension.

Referring to FIGS. 7 and 8, the upper and lower sections of knee 60 are interconnected using a series of bars 19, each of which is coupled to each of the upper and lower section of knee 60 using corresponding pairs of attachment points 14, so that the upper and lower section of knee 60 can articulate through the conventional knee positions of flexion, mid-flexion, and extension. Upper and lower sections of knee 60 are formed to include a planar surface 15 for fastening to a lower limb system, such as that described herein, whether machined or 3D printed. As further seen in FIGS. 7 and 8, channels 17 in the upper and lower section of knee 60 may be associated with the central bar 10 to increase the range of motion of prosthetic knee 60 by allowing for further bending motion. Insertion sites 18 for interconnection to the machined components of a lower limb system, whether machined or 3D printed, may also be provided in association with planar surfaces 15. Referring to FIG. 9, the positions of bars 19 of knee 60 are shown in more detail along with a recess 20 for housing assistive mechanism that aids in the flexion and extension of the prosthetic knee.

FIG. 10 demonstrates a cross sectional view of the preferred embodiment of the 3D printed modular prosthetic knee having predetermined fiber routing patterns 21. The fiber may follow a concentric pattern, and may serve to increase the durability and strength of the susceptible bodies of the modular prosthetic knee component.

FIG. 11 demonstrates a cross sectional view of a preferred embodiment of the 3D printed modular prosthetic knee, and further highlights recesses for a mechanism for assistance in flexion and extension.

FIG. 12 demonstrates a cross sectional view of a bar that may constitute the flexion and extension features of the preferred embodiment, and may fasten the upper and lower sections of the embodiment with machined components for system assembly. A concentric fiber routing pattern 22 that aids in structural integrity and strength is illustrated.

There is seen in FIGS. 13 and 14 an embodiment of a 3D printed prosthetic pylon 32. Pylon 32 may be printed with fiber composite, stainless steel, or titanium in the longitudinal direction, and continuous fiber material may be included in concentric rings tracing the interior of the embodiment. Internal reinforcement structure 23 and associated channels 24 may be included for reduced weight. Pylon 32 may also include a flat portion 25 for ease in printing. As seen in the cross-section of FIG. 15, pylon 32 may include internal concentric fiber reinforcement 26.

Referring to FIGS. 16 and 17, an above-knee lower limb prosthetic system 70 may include foot 50, knee 60 and pylon 32 described above. System 70 includes an above-knee socket 27 along with a female pyramid adapter 29 and a male pyramid adapter 30 coupled to planar surface 15 of the upper section of knee 60. Corresponding planar surface of lower section of knee 60 is coupled to pylon 32 via pyramid adapter 29 and tube clamp 33. Pylon 32 may then be, in turn, coupled to foot 50 via a tube clamp 33 and a pyramid adapter 30 that mounts to channels 2 and insertion sites 8 of foot 50.

Referring to FIGS. 18 and 19, a below-knee lower limb prosthetic system 80 may omit the above-knee socket 25 and knee 60, and instead include a below-knee socket 26 coupled to a pylon 32 and foot 50 using tube clamps 33 and pyramid adapters 30.

An embodiment of an above-knee socket 82 that may be 3D printed using CFF is exhibited in FIG. 20. An embodiment of a below-knee socket 84 that may be 3D printed using CFF is exhibited in FIG. 21.

The aforementioned components may be 3D printed with composite fiber reinforcement, may be 3D printed with stainless steel or titanium, or may integrate with components belonging to traditionally manufactured prosthetic systems. The 3D printed lower limb prosthetic device may be comprised of a foot, an anatomical foot shell, a male pyramid adapter, a female pyramid adapter, a tube clamp, a pylon, a knee, a socket, machined components utilized for system assembly, a cable extension locking mechanism and flexion assist routing materials utilized within the knee embodiment. The materials included in these embodiments may be formed of nylon, with fiber reinforcement included in some capacity. Other embodiments may be formed of, or include, metal, composite material, or noise dampening material. The metal may be titanium or steel, and the composite material may be a fusion of plastics and carbon fiber or fiberglass. In some of the embodiments of the prosthetic components, the fiber may be laid in specific patterns to reinforce specific areas of the embodiment, or the fiber may be distributed evenly to create a uniform composite material throughout the embodiment. The embodiments of the components may be specifically designed to enable DER, and may be post processed to add additional durability and longevity to the specific component.

What is claimed is:

1. A prosthetic, comprising:
   a plurality of layers that are stacked in abutment with each other so that each layer is aligned in parallel along a common plane to build up a three-dimensional body, wherein the body comprises a foot having a heel and a forefoot interconnected to the heel by a curved portion; wherein each layer of the plurality of layers of the body comprises a series of boundary rings that are positioned concentrically and in abutment with each other so that an outside of each ring of the series of boundary rings is abutting the outside of another ring of the series of boundary rings to build each of the plurality of layers; and
   wherein each boundary ring of the series of concentric boundary rings is formed from a single continuous composite fiber.

2. The prosthetic of claim 1, wherein the body includes a core surrounded by the series of boundary rings.

3. The prosthetic of claim 2, wherein the series of boundary rings comprises at least six rings positioned concentrically and adjacently to each other.

4. The prosthetic of claim 3, wherein the body includes a mounting portion configured for attachment to a component of a prosthetic system.

5. The prosthetic of claim 4, wherein the mounting portion comprises a pair of passages extending laterally through the body and a series of openings extending transversely to and in communication with the pair of passages.

6. The prosthetic of claim 5, wherein the mounting portion is interconnected to the heel and forefoot by a second curved portion.

7. The prosthetic of claim 5, wherein the body comprises a pair of corresponding knee sections, wherein one of the pair of corresponding knee sections includes the mounting portion and the other of the pair of corresponding knee sections includes a second mounting portion.

8. The prosthetic of claim 7, wherein the pair of knee sections are interconnected by a four bar mechanism.

9. The prosthetic of claim 8, wherein the pair of knee sections include a cable flexion inhibitor extending therebetween and embedded therein.

10. The prosthetic of claim 5, wherein the body comprises a pylon and the series of concentric layers extending longitudinally within the pylon.

11. The prosthetic of claim 10, further comprising a socket interconnected to the pylon.

12. A prosthetic system, comprising:
    a foot formed from a first plurality of layers stacked in abutment with each other so that each layer of the foot is aligned in parallel along a first common plane to build up a three-dimensional body, wherein each layer of the plurality of layers of the body comprises a first series of concentric boundary rings that are positioned concentrically and in abutment with each other so that an outside of each ring of the series of boundary rings abuts the outside of another ring of the series of boundary rings to build such layer and each boundary ring of the first series of boundary rings is formed from a single continuous composite fiber, wherein the foot has a first mounting portion; and
    a pylon formed from a second plurality of layers stacked adjacently to each other so that each layer of the body is aligned along a second common plane, wherein each layer of the second plurality of layers of the pylon comprises a second series of concentric boundary rings that are positioned concentrically and in abutment with each other so that an outside of each ring of the second series of boundary rings is adjacent to and abuts the outside of another ring of the second series of boundary rings to build each of the plurality of layers, wherein each of the second series of boundary rings is formed from a single continuous composite fiber, wherein the pylon is interconnected to the first mounting portion.

13. The system of claim 12, further comprising a socket interconnected to the pylon.

14. The system of claim 12, further comprising a pair of knee sections, wherein one of the pair of knee sections is interconnected to the pylon.

15. The system of claim 14, further comprising a socket interconnected to the other of the knee sections.

16. The system of claim 15, wherein the pair of knee sections are interconnected by a four bar mechanism.

17. The system of claim 16, wherein the pair of knee sections include a cable flexion inhibitor embedded therein.

* * * * *